(12) United States Patent
Bi et al.

(10) Patent No.: US 11,892,384 B2
(45) Date of Patent: Feb. 6, 2024

(54) EVALUATION METHOD OF MIXING UNIFORMITY OF COMPOSITE POWDER

(71) Applicant: INSTITUTE OF FOOD SCIENCE AND TECHNOLOGY, CHINESE ACADEMY OF AGRICULTURAL SCIENCES, Beijing (CN)

(72) Inventors: Jinfeng Bi, Beijing (CN); Qinqin Chen, Beijing (CN); Xinye Wu, Beijing (CN); Xing Zhang, Xinle (CN); Jian Lyu, Beijing (CN); Ying Lyu, Shenyang (CN)

(73) Assignee: INSTITUTE OF FOOD SCIENCE AND TECHNOLOGY, CHINESE ACADEMY OF AGRICULTURAL SCIENCES, Beijing (CN)

(*) Notice: Subject to any disclaimer, the term of this patent is extended or adjusted under 35 U.S.C. 154(b) by 0 days.

(21) Appl. No.: 17/758,397

(22) PCT Filed: Nov. 18, 2020

(86) PCT No.: PCT/CN2020/129692
§ 371 (c)(1),
(2) Date: Jul. 5, 2022

(87) PCT Pub. No.: WO2022/099732
PCT Pub. Date: May 19, 2022

(65) Prior Publication Data
US 2023/0266212 A1 Aug. 24, 2023

(30) Foreign Application Priority Data

Nov. 10, 2020 (CN) .......................... 202011248647.8

(51) Int. Cl.
*G01N 1/38* (2006.01)

(52) U.S. Cl.
CPC ..................................... *G01N 1/38* (2013.01)

(58) Field of Classification Search
CPC .......... G01N 1/38; G01N 33/02; G01N 11/14; G01N 33/025
See application file for complete search history.

(56) References Cited

FOREIGN PATENT DOCUMENTS

| CN | 10393539 A | 8/2014 |
|---|---|---|
| CN | 106404584 A | 2/2017 |

(Continued)

OTHER PUBLICATIONS

Baoshen Hu, Statistical paragraph 1 of section 3.3.1 of p. 47, paragraphs 1-3 of section 3.3.2 of p. 48 Dec. 31, 2001.

*Primary Examiner* — David Z Huang
(74) *Attorney, Agent, or Firm* — CBM PATENT CONSULTING, LLC

(57) ABSTRACT

An evaluation method of mixing uniformity of composite powder includes: determining raw materials of composite powder to be evaluated and mass ratio; mixing to obtain multiple standard composite powder with different mixing time; determining flow energy of each standard composite powder; analyzing the flow energy of multiple standard composite powders by significant difference method, determining at least 3 consecutive standard composite powders with no significant difference in flow energy according to mixing time from small to large, defining as uniform-mixed standard composite powder, calculating average value of flow energy of uniform-mixed standard composite powder, and recording as standard flow energy $TFE_s$; determining the flow energy of composite powder to be evaluated, calculating percentage difference $P \cdot V_{ds}$ between $TFE_d$ and $TFE_s$, and evaluating mixing uniformity of composite powder according to $P \cdot V_{ds}$.

4 Claims, 1 Drawing Sheet

(56) References Cited

FOREIGN PATENT DOCUMENTS

| | | |
|---|---|---|
| CN | 107727534 A | 2/2018 |
| CN | 108106968 A | 6/2018 |
| CN | 109490156 A | 3/2019 |
| CN | 111175449 A | 5/2020 |
| CN | 111721715 A | 8/2020 |

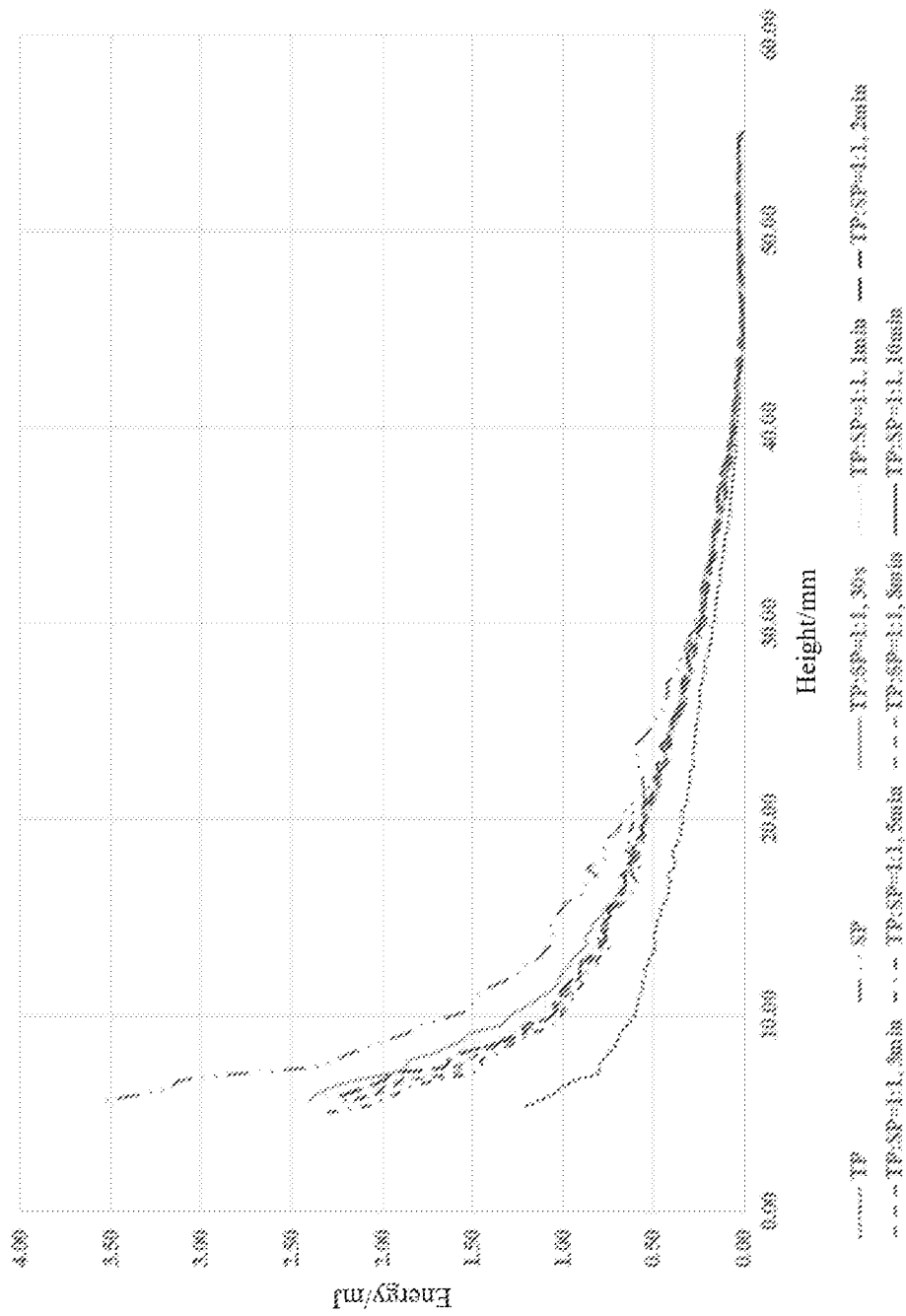

EVALUATION METHOD OF MIXING UNIFORMITY OF COMPOSITE POWDER

TECHNICAL FIELD

The present disclosure relates to the technical field of evaluation of mixing uniformity. More specifically, the present disclosure relates to an evaluation method of mixing uniformity of composite powder.

BACKGROUND

Currently, powder products are the most widely used in raw materials and product forms, which can be up to more than 70%.

With the improvement of people's living standards and the increasing demand for nutrition and health, wherein, composite fruit and vegetable powder is favored by consumers due to its good physiological activity and rich nutritional value. The mixing uniformity of the composite fruit and vegetable powder is a core factor that affects the distribution of nutritional functional components and product quality. The mixing uniformity of powder is currently determined by chloride ionic-selective electrode method, methyl violet method, particle size distribution method, near infrared spectroscopy method, etc., wherein the chloride ionic-selective electrode method is a chemical determination method that is relatively time-consuming and labor-intensive, the methyl violet method is not suitable for mixing colored materials and is easy to cause material pollution, and the particle size distribution method and the near infrared spectroscopy method mostly adopts modem analysis equipment for determination, which has high equipment cost, and long sample processing and determination cycle. Therefore, a determination method that is convenient, rapid and universal needs to be developed urgently.

SUMMARY

An object of the present disclosure is to solve at least the above problems and to provide at least advantages that will be described hereinafter.

Another object of the present disclosure is to provide an evaluation method of mixing uniformity of composite powder, which is convenient, rapid and universal to evaluate the mixing uniformity of composite powder.

In order to achieve these objects and other advantages according to the present disclosure, an evaluation method of mixing uniformity of composite powder is provided, including the following steps:

S1, determining the raw materials of composite powder to be evaluated and a mass ratio of each raw material according to the composite powder to be evaluated;

S2, mixing the raw materials according to the amount ratio to obtain multiple standard composite powders with different mixing time, wherein a mixing time difference between any two adjacent standard composite powders is not be less than 30 s and not more than 5 min according to the mixing time from small to large;

S3, determining the flow energy of each standard composite powder;

S4, analyzing and comparing the flow energy of the multiple standard composite powders by a significant difference method, determining at least 3 consecutive standard composite powders with no significant difference in the flow energy according to the mixing time from small to large, defining as uniform-mixed standard composite powder, calculating an average value of the flow energy of the uniform-mixed standard composite powder, and recording as standard flow energy: $TFE_s$;

S5, determining the flow energy of the composite powder to be evaluated, calculating a percentage difference $P \cdot V_{ds}$ between $TFE_d$ and $TFE_s$ according to $P \cdot V_{ds} = |(TFE_d - TFE_s)|/TFE_s * 100$, and evaluating the mixing uniformity of the composite powder according to $P \cdot V_{ds}$.

Preferably, a preparation method of each standard composite powder in S2 includes: placing the raw materials according to the mass ratio in a Turbula three-dimensional mixer, and mixing it for preset time, wherein a mixing speed is 22-96 rpm;

The mixing time difference between any two adjacent standard composite powders is not more than 3 min, and the minimum mixing time is 30 s.

Preferably, a specific process of determining flow energy of each standard composite powder in S3 and determining flow energy of the composite powder to be evaluated in S5 includes the following steps:

S3a, placing the composite powder to be determined in a container of a powder analyzer and cutting it to obtain volume-fixed composite powder to be determined;

S3b, a propeller rotating deeply from a surface layer of the volume-fixed composite powder to be determined, recording a height H of the propeller entering the composite powder to be determined in real time, and determining flow energy $TFE_H$ of composite powder to be determined at corresponding height, wherein the propeller rotates anticlockwise at an angle of +5 to 10°, and a speed of the propeller is 5-100 mm/s;

S3c, calculating the flow energy $\int_0^H (TFE_H) \, dH$ of the composite powder to be determined.

Preferably, wherein the container in S3a is a cylindrical container, before cutting, the propeller of the powder analyzer rotating deeply from the surface layer to the bottom of the composite powder to be determined, and then rotating from the bottom to the surface layer to the bottom of the composite powder to be determined, wherein the propeller rotates clockwise at an angle of −2 to −5°, and a speed of the propeller is 5-100 mm/s.

Preferably, the flow energy $TFE_H$ of composite powder to be determined at corresponding height is:

$$TFE_H = \frac{T}{R \tan \alpha} + F_{base},$$

wherein T is a torque, R is a propeller radius, α is a helix angle, and $F_{base}$ is an acting force of propeller perpendicular to the bottom of the composite powder to be determined.

Preferably, wherein evaluating the mixing uniformity of the composite powder according to the $P \cdot V_{ds}$ includes: if $P \cdot V_{ds}$ does not exceed 5%, the composite powder to be evaluated is uniformly mixed.

The present disclosure at least includes the following advantageous effects:

The evaluation method of mixing uniformity of composite powder of the present disclosure can be used for evaluating the mixing uniformity of composite powder, is convenient, rapid, and has high universality.

Other advantages, objects and features of the present disclosure will be partially reflected by the following description, and will be partially understood by those skilled in the art through researching and practicing the present disclosure.

BRIEF DESCRIPTION OF THE DRAWINGS

FIG. 1 is a dynamic change curve diagram of the height and flow energy of TP and SP composite powder at different mixing times according to one embodiment of the present disclosure.

DETAILED DESCRIPTION

The present disclosure will be further described in detail hereinafter with reference to the accompanying drawings, so that those skilled in the art can implement the present disclosure with reference to the specification.

Embodiment 1

An evaluation method of mixing uniformity of composite powder includes the following steps:

S1, selecting the composite fruit-vegetable powder as composite powder to be evaluated, including tomato powder (TP) with single raw material and spinach powder (SP) with single raw material, wherein a mass ratio of TP and SP is 1:1;

S2, mixing TP and SP according to a mass ratio of 1:1 with a Turbula three-dimensional mixer to obtain 7 standard composite powders with different mixing time, wherein the mixing time from small to large is 30 s, 1 min, 2 min, 3 min, 5 min, 8 min and 10 min, one standard composite powder is obtained at each mixing time, and a mixing speed is 72 rpm;

S3, determining the flow energy of each standard composite powder, specifically including:

S3a, placing the standard composite powder to be determined in a cylindrical container of a powder analyzer, a propeller of the powder analyzer rotating deeply from the surface layer to the bottom of the standard composite powder to be determined, then rotating from the bottom to the surface layer of the standard composite powder to be determined, wherein the propeller rotates clockwise at an angle of −2°, and a speed of the propeller is 5 mm/s;

performing quantitative cutting with a cutting device at an upper end of the cylindrical container to make a surface layer of the standard composite powder to be determined in each cylindrical container be even with a plane of an opening of the cylindrical container so that the standard composite powder to be determined is in a fixed volume to obtain volume-fixed standard composite powder, wherein a fixed volume is 25 mL;

S3b, the propeller rotating deeply from the surface layer of the volume-fixed standard composite powder, recording a height H of the propeller entering the volume-fixed standard composite powder in real time, and determining the flow energy $TFE_H$ of the volume-fixed standard composite powder at corresponding height, wherein the propeller rotates anticlockwise at an angle of +5°, a speed of the propeller is 100 mm/s, and a height range is 5-55 mm, wherein $$TFE_H = \frac{T}{R \tan \alpha} + F_{base},$$

T is a torque, R is a propeller radius (a propeller radius of 25 mL is 11.8 mm), α is a helix angle, and $F_{base}$ is an acting force of propeller perpendicular to the bottom of the standard composite powder to be determined;

wherein a drawn curve with H as the abscissa and $TFE_H$ as the ordinate is as shown in FIG. 1;

S3c, calculating the flow energy $\int_0^H (TFE_H) \, dH$ of the standard composite powder to be determined;

S4, using single raw material as control groups, analyzing and comparing the flow energy of 2 control groups and 7 standard composite powders by significant difference method, determining at least 3 consecutive standard composite powders with no significant difference in the flow energy according to the mixing time from small to large, defining as uniform-mixed standard composite powder, calculating an average value of the flow energy of the uniform-mixed standard composite powder, and recording as standard flow energy: $TFE_s$;

S5, determining the flow energy of the composite powder to be evaluated A, calculating a percentage difference $P \cdot V_{ds}$ between $TFE_d$ and $TFE_s$ according to $P \cdot V_{ds} = |(TFE_d - TFE_s)|/TFE_s * 100$, if $P \cdot V_{ds}$ does not exceed 5%, the composite powder to be evaluated A being uniformly mixed, as shown in Table 1.

TABLE 1

Change of total flow energy of the composite powder (TP:SP = 1:1) under different mixing time

| Sample | Flow energy | Percentage difference P.V (%) | Mixing uniformity |
|---|---|---|---|
| TP (control group) | 105.46 ± 0.76a | / | / |
| SP (control group) | 35.70 ± 0.41f | / | / |
| TP:SP = 1:1, 30 s | 77.69 ± 2.70b | 31.50 | nonuniform |
| TP:SP = 1:1, 1 min | 67.99 ± 2.25c | 15.07 | nonuniform |
| TP:SP = 1:1, 2 min | 62.20 ± 0.45d | 5.26 | nonuniform |
| TP:SP = 1:1, 3 min | 59.06 ± 0.28e | 0.05 | uniform |
| TP:SP = 1:1, 5 min | 59.85 ± 1.93e | 1.29 | uniform |
| TP:SP = 1:1, 8 min | 58.99 ± 0.40e | 0.17 | uniform |
| TP:SP = 1:1, 10 min | 58.44 ± 1.13e | 1.09 | uniform |

It can be seen from the Table 1 and FIG. 1 that the flow energy of TP and SP composite powder after mixing is within a range of the flow energy of single powder of TP and SP. With the prolonging of mixing time, the total flow energy of the composite powder firstly shows a decreasing trend and then a stabilizing trend. Specifically, the total flow energy of the composite powder is gradually stabilized after mixing TP and SP for 3 min, which is no significant difference with the total flow energy of the composite powder after mixing for 10 min. Therefore, the standard composite powder with mixing time of 3 min, 5 min, 8 min and 10 min is defined as the uniform-mixed standard composite powder, an average value $TFE_s$ of the flow energy of the uniform-mixed standard composite powder at four time points is calculated, and a percentage difference $P \cdot V_{ds}$, between the flow energy $TFE_d$ of the composite powder to be evaluated A and $TFE_s$ according to $P \cdot V_{ds} = (TFE_d - TFE_s)/TFE_s * 100$ is calculated, wherein, if $P \cdot V_{ds}$ is more than 5%, the composite powder has not been uniformly mixed, and if $P \cdot V_{ds}$, does not exceed 5%, the composite powder has been uniformly mixed.

Embodiment 2

An evaluation method of mixing uniformity of composite powder includes the following steps:

S1, selecting composite fruit-vegetable powder as composite powder to be evaluated, including apple powder (AP)

with single raw material and spinach powder (SP) with single raw material, wherein a mass ratio of AP and SP is 2:1;

S2, mixing AP and SP according to a mass ratio of 2:1 with a Turbula three-dimensional mixer to obtain 7 standard composite powders with different mixing time, wherein the mixing time from small to large is 30 s, 1 min, 2 min, 3 min, 5 min, 8 min and 10 min, one standard composite powder is obtained at each mixing time, and a mixing speed is 96 rpm;

S3, determining the flow energy of each standard composite powder, specifically including:

S3a, placing the standard composite powder to be determined in a cylindrical container of a powder analyzer, a propeller of the powder analyzer rotating deeply from the surface layer to the bottom of the standard composite powder to be determined, then rotating from the bottom to the surface layer of the standard composite powder to be determined, wherein the propeller rotates clockwise at an angle of −3°, and a speed of the propeller is 40 mm/s;

performing quantitative cutting with a cutting device at the upper end of the cylindrical container to make a surface layer of the standard composite powder to be determined in each cylindrical container be even with a plane of an opening of the cylindrical container so that the standard composite powder to be determined is in a fixed volume to obtain volume-fixed standard composite powder, wherein a fixed volume is 50 mL;

S3b, the propeller rotating deeply from the surface layer of the volume-fixed standard composite powder, recording a height H of the propeller entering the volume-fixed standard composite powder in real time, and determining the flow energy $TFE_H$ of the volume-fixed standard composite powder at corresponding height, wherein the propeller rotates anticlockwise at an angle of +5°, a speed of the propeller is 40 mm/s, and a height range is 5-55 mm, wherein $$TFE_H = \frac{T}{R \tan \alpha} + F_{base},$$

T is a torque, R is a propeller radius (a propeller radius of 50 mL is 24 mm), α is a helix angle, and $F_{base}$ is an acting force of propeller perpendicular to the bottom of the standard composite powder to be determined;

wherein a drawn curve with H as the abscissa and $TFE_H$ as the ordinate is drawn;

S3c, calculating the flow energy $\int_0^H (TFE_H) \, dH$ of the standard composite powder to be determined;

S4, using single raw material as control groups, analyzing and comparing the flow energy of 2 control groups and 7 standard composite powders by a significant difference method, determining at least 3 consecutive standard composite powders with no significant difference in the flow energy according to the mixing time from small to large, defining as uniform-mixed standard composite powder, calculating an average value of the flow energy of the uniform-mixed standard composite powder, and recording as standard flow energy: $TFE_s$;

S5, determining the flow energy of the composite powder to be evaluated B, calculating a percentage difference $P \cdot V_{ds}$ between $TFE_d$ and $TFE_s$ according to $P \cdot V_{ds} = |(TFE_d - TFE_s)|/TFE_s * 100$, if $P \cdot V_{ds}$ does not exceed 5%, the composite powder to be evaluated B being uniformly mixed, as shown in Table 2.

TABLE 2

Change of total flow energy of the composite powder (AP:SP = 2:1) under different mixing time

| Sample | Flow energy | Percentage difference P.V (%) | Mixing uniformity |
| --- | --- | --- | --- |
| AP (control group) | 170.10 ± 2.91a | / | / |
| SP (control group) | 50.12 ± 0.26g | / | / |
| AP:SP = 2:1, 30 s | 139.62 ± 3.19b | 29.42 | nonuniform |
| AP:SP = 2:1, 1 min | 127.86 ± 0.99c | 18.52 | nonuniform |
| AP:SP = 2:1, 2 min | 117.89 ± 0.89d | 9.28 | nonuniform |
| AP:SP = 2:1, 3 min | 114.58 ± 0.98e | 6.21 | nonuniform |
| AP:SP = 2:1, 5 min | 109.03 ± 1.09f | 1.07 | uniform |
| AP:SP = 2:1, 8 min | 106.85 + 1.18f | 0.95 | uniform |
| AP:SP = 2:1, 10 min | 107.77 + 1.93f | 0.10 | uniform |

It can be seen from the Table 2 that the flow energy of AP and SP composite powder after mixing is within a range of the flow energy of single powder of AP and SP, and, with the prolonging of mixing time, the total flow energy of the composite powder firstly shows a decreasing trend and then stabilizing trend. Specifically, the total flow energy of the composite powder is gradually stabilized after mixing AP and SP for 5 min, which is no significant difference with the total flow energy of the composite powder after mixing for 10 min. Therefore, the standard composite powder with mixing time of 5 min, 8 min and 10 min is defined as the uniform-mixed standard composite powder, an average value $TFE_s$ of the flow energy of the uniform-mixed standard composite powder at three time points is calculated, and a percentage difference $P \cdot V_{ds}$ between the flow energy $TFE_d$ of the composite powder to be evaluated B and $TFE_s$ according to $P \cdot V \& = (TFE_d - TFE_s)|/TFE_s * 100$ is calculated, wherein, if $P \cdot V_{ds}$, is more than 5%, the composite powder has not been uniformly mixed, and if $P \cdot V_{ds}$ does not exceed 5%, the composite powder has been uniformly mixed.

Embodiment 3

An evaluation method of mixing uniformity of composite powder includes the following steps:

S1, selecting composite fruit-vegetable powder as composite powder to be evaluated, including tomato powder (TP) with single raw material and spinach powder (SP) with single raw material, wherein a mass ratio of TP and SP is 3:2;

S2, mixing TP and SP according to a mass ratio of 3:2 with a Turbula three-dimensional mixer to obtain 6 standard composite powders with different mixing time, wherein the mixing time from small to large is 30 s, 1 min, 2 min, 3 min, 5 min, 8 min, one standard composite powder is obtained at each mixing time, and a mixing speed is 22 rpm;

S3, determining the flow energy of each standard composite powder, specifically including:

S3a, placing the standard composite powder to be determined in a cylindrical container of a powder analyzer, a propeller of the powder analyzer rotating deeply from the surface layer to the bottom of the standard composite powder to be determined, then rotating from the bottom to the surface layer of the standard composite powder to be determined, wherein the propeller rotates clockwise at an angle of −5°, and a speed of the propeller is 100 mm/s;

performing quantitative cutting with a cutting device at the upper end of the cylindrical container to make a surface layer of the standard composite powder to be determined in each cylindrical container be even with a plane of an opening of the cylindrical container so that the standard composite powder to be determined is in a fixed volume to obtain volume-fixed standard composite powder, wherein a fixed volume is 25 mL;

S3b, the propeller rotating deeply from the surface layer of the volume-fixed standard composite powder, recording a height H of the propeller entering the volume-fixed standard composite powder in real time, and determining flow energy $TFE_H$ of volume-fixed standard composite powder at corresponding height, wherein the propeller rotates anticlockwise at an angle of +10°, a speed of the propeller is 5 mm/s, and a height range is 5-55 mm, wherein $$TFE_H = \frac{T}{R \tan \alpha} + F_{base},$$

T is a torque, R is a propeller radius (a propeller radius of 25 mL is 11.8 mm), α is a helix angle, and $F_{base}$ is an acting force of propeller perpendicular to the bottom of the standard composite powder to be determined;

S3c, calculating the flow energy $\int_0^H (TFE_H) \, dH$ of the standard composite powder to be determined;

S4, analyzing and comparing the flow energy of 6 standard composite powders by a significant difference method, determining at least 3 consecutive standard composite powders with no significant difference in the flow energy according to the mixing time from small to large, defining as uniform-mixed standard composite powder, calculating an average value of the flow energy of the uniform-mixed standard composite powder, and recording as standard flow energy: $TFE_s$;

S5, determining the flow energy of the composite powder to be evaluated XX, calculating a percentage difference $P \cdot V_{ds}$ between $TFE_d$ and $TFE_s$ according to $P \cdot V_{ds} = |(TFE_d - TFE_s)|/TFE_s * 100$, if $P \cdot V_{ds}$ does not exceed 5%, the composite powder to be evaluated XX being uniformly mixed, as shown in Table 3.

TABLE 3

Change of total flow energy of the composite powder (TP:SP = 3:2) under different mixing time

| Sample | Flow energy | Percentage difference P.V (%) | Mixing uniformity |
|---|---|---|---|
| TP:SP = 3:2, 30 s | 189.50 ± 0.69a | 26.48 | nonuniform |
| TP:SP = 3:2, 1 min | 172.40 ± 0.48b | 15.06 | nonuniform |
| TP:SP = 3:2, 2 min | 151.75 ± 0.37c | 1.28 | uniform |
| TP:SP = 3:2, 3 min | 151.63 ± 1.27c | 1.20 | uniform |
| TP:SP = 3:2, 5 min | 148.71 ± 1.57c | 0.74 | uniform |
| TP:SP = 3:2, 8 min | 147.21 ± 2.82c | 1.74 | uniform |

It can be seen from the Table 3 that the total flow energy of TP and SP composite powder after mixing firstly shows a decreasing trend and then stabilizing trend. Specifically, the total flow energy of the composite powder is gradually stabilized after mixing TP and SP for 2 min, which is no significant difference with the total flow energy of the composite powder after mixing for 8 min. Therefore, the standard composite powder with mixing time of 2 min, 3 min, 5 min and 8 min is defined as the uniform-mixed standard composite powder, an average value $TFE_s$ of the flow energy of the uniform-mixed standard composite powder at four time points is calculated, and a percentage difference $P \cdot V_{ds}$ between the flow energy $TFE_d$ of the composite powder to be evaluated and $TFE_s$ according to $P \cdot V_{ds} = (TFE_d - TFE_s)/TFE_s * 100$ is calculated, wherein, if $P \cdot V_{ds}$ is more than 5%, the composite powder has not been uniformly mixed, and if $P \cdot V_{ds}$ does not exceed 5%, the composite powder has been uniformly mixed.

Verification Experiment 1

Selecting the standard composite powder with mixing time of 1 min and 3 min in Embodiment 1;

Determining the red-green "a*" value of 10 different parts of each standard composite powder with an electronic eye, evaluating the mixing uniformity of the standard composite powder according to coefficient of variation (CV) of determined data of the 10 different parts, wherein, if CV does not exceed 10%, the composite powder has been uniformly mixed, and if CV is more than 10%, the composite powder has not been uniformly mixed.

TABLE 4

Color change of the composite powder (TP:SP = 1:1) under different mixing time

| Sample | a* average value | Standard deviation | Coefficient of variation (CV) (%) | Mixing uniformity |
|---|---|---|---|---|
| TP:SP = 1:1, 1 min | 6.04 | 0.96 | 15.9 | nonuniform |
| TP:SP = 1:1, 3 min | 5.13 | 0.21 | 4.1 | uniform |

It can be seen from the Table 4 that the coefficient of variation (CV) of color a* value of the TP and SP composite powder after mixing for 1 min according to color mixing uniformity as an evaluation standard is 15.9%, which is more than 10%, and shows that the composite powder is in a nonuniformity state. The coefficient of variation (CV) of color a* value of the TP and SP composite powder after mixing for 3 min is 4.1%, which is less than 10%, and shows that the composite powder is in a uniformity state. The evaluation results are consistent with the evaluation standard of the corresponding mixing conditions in Table 1.

Although the embodiments of the present disclosure have been disclosed as above, the present disclosure is not limited to the applications listed in the specification and the implementations. It can be applied to various fields suitable for the present disclosure absolutely, and other modifications can be easily realized by those skilled in the art. Therefore, the present disclosure is not limited to the specific details and the illustrations shown and described herein without departing from the general concepts defined by the claims and equivalent scopes.

What is claimed is:

1. An evaluation method of mixing uniformity of composite powder, including the following steps:
    S1, determining raw materials of composite powder to be evaluated and a mass ratio of each raw material according to the composite powder to be evaluated;
    S2, mixing the raw materials according to the mass ratio to obtain multiple standard composite powders with different mixing times, wherein a mixing time difference between any two adjacent standard composite powders according to the mixing time from small to large is not be less than 30 s and not more than 3 min;
    S3, determining the flow energy of each standard composite powder;
    S4, analyzing and comparing the flow energy of the multiple standard composite powders by a significant difference method, determining at least 3 consecutive standard composite powders with no significant difference in the flow energy according to the mixing time from small to large, defining each of the at least 3 consecutive standard composite powders as uniform-mixed standard composite powder, calculating an average value of the flow energy of the uniform-mixed standard composite powders, and record the average value as standard flow energy: $TFE_s$;

S5, determining the flow energy of the composite powder to be evaluated: $TFE_d$, calculating a percentage difference $P \cdot V_{ds}$ between $TFE_d$ and $TFE_s$ according to $P \cdot V_{ds} = |(TFE_d - TFE_s)|/TFE_s *100$, and evaluating the mixing uniformity of the composite powder according to $P \cdot V_{ds}$;

wherein a specific preparation method of each standard composite powder in S2 includes: placing the raw materials according to the mass ratio in a Turbula three-dimensional mixer, and mixing it for preset time, wherein a mixing speed is 22-96 rpm;

wherein evaluating the mixing uniformity of the composite powder according to the $P \cdot V_{ds}$ includes: if $P \cdot V_{ds}$ does not exceed 5%, the composite powder to be evaluated is determined to be uniformly mixed.

2. The evaluation method of mixing uniformity of composite powder according to claim 1, wherein a specific process of determining flow energy of each standard composite powder in S3 and determining flow energy of the composite powder to be evaluated in S5 includes the following steps:

S3a, placing the composite powder to be determined in a container of a powder analyzer and cutting it to obtain volume-fixed composite powder to be determined;

S3b, placing a propeller rotating deeply from a surface layer of the volume-fixed composite powder to be determined, recording a height H of the propeller entering the composite powder to be determined in real time, and determining flow energy $TFE_H$ of the composite powder to be determined at corresponding height, wherein the propeller rotates anticlockwise at an angle of +5 to 10°, and a speed of the propeller is 5-100 mm/s;

S3c, calculating the flow energy $\int_0^H (TFE_H)dH$ of the composite powder to be determined.

3. The evaluation method of mixing uniformity of composite powder according to claim 1, wherein the container in S3a is a cylindrical container, before cutting, the propeller of the powder analyzer rotating deeply from the surface layer to a bottom of the composite powder to be determined, and then rotating from the bottom to the surface layer to the bottom of the composite powder to be determined, wherein the propeller rotates clockwise at an angle of −2 to −5°, and a speed of the propeller is 5-100 mm/s.

4. The evaluation method of mixing uniformity of composite powder according to claim 1, wherein the flow energy $TFE_H$ of the composite powder to be determined at corresponding height is:

$$TFE_H \frac{T}{R \tan \alpha} + F_{base},$$

wherein T is a torque, R is a propeller radius, α is a helix angle, and $F_{base}$ is an acting force of propeller perpendicular to the bottom of the composite powder to be determined.

* * * * *